United States Patent [19]
Ōmura et al.

[11] Patent Number: 6,077,943
[45] Date of Patent: Jun. 20, 2000

[54] METHOD OF PRODUCING ERYTHROMYCIN DERIVATIVE

[75] Inventors: Satoshi Ōmura, Tokyo; Masayasu Kato, Hyogo; Miichiro Arita, Nara, all of Japan

[73] Assignees: Takeda Chemical Industries, Ltd., Osaka; The Kitasato Institute, Tokyo, both of Japan

[21] Appl. No.: 09/143,365

[22] Filed: Aug. 28, 1998

Related U.S. Application Data

[63] Continuation of application No. PCT/JP97/00605, Feb. 28, 1997.

[30] Foreign Application Priority Data

Mar. 1, 1996 [JP] Japan ................. 8-045059

[51] Int. Cl.$^7$ ................. A01N 43/04; C07H 1/06
[52] U.S. Cl. ................. 536/7.2; 514/29; 536/127
[58] Field of Search ................. 514/29; 536/7.2, 536/127

[56] References Cited

U.S. PATENT DOCUMENTS

| | | | |
|---|---|---|---|
| 5,175,150 | 12/1992 | Omura et al. | 514/29 |
| 5,418,224 | 5/1995 | Hoeltje et al. | 514/28 |
| 5,470,961 | 11/1995 | Harada et al. | 536/7.4 |
| 5,658,888 | 8/1997 | Koga et al. | 514/29 |

FOREIGN PATENT DOCUMENTS

| | | |
|---|---|---|
| 0 561 413 A1 | 9/1993 | European Pat. Off. |
| 93/24509 | 12/1993 | WIPO |
| 94/10185 | 5/1994 | WIPO |
| 97/31930 | 9/1997 | WIPO |

OTHER PUBLICATIONS

Tsuzuki et al., "Motilides, Macrolides with Gastrointestinal Motor Stimulating Activity. I. O–Substituted and Tertiary N–Substituted Derivatives of 8,9–Anhydroerythromycin A 6,9–Hemiacetal", Chem. Pharm. Bull., 37(10): 2687–1700, 1989.

Lartey et al., "Synthesis of 4"–Deoxy Motilides: Identification of a Potent and Orally Active Prokinetic Drug Candidate, J. Med. Chem., vol. 38: 1793–1798, 1995.

Koga et al., Bioorganic & Medicinal Chemistry Letters, vol. 5 No. 8, pp. 835–838 (1995).

*Primary Examiner*—Howard C. Lee
*Attorney, Agent, or Firm*—Wenderoth, Lind & Ponack, L.L.P.

[57] ABSTRACT

A method of producing an N-demethyl-N-isopropyl-8,9-anhydroerythromycin A-6,9-hemiacetal or a salt thereof, characterized in that an N-demethylerythromycin A or a salt thereof is reacted with an isopropylating agent and subsequently treated under acidic conditions, and a method of producing a substantially pure crystal of an 8,9-anhydroerythromycin A-6,9-hemiacetal derivative represented formula (VI):

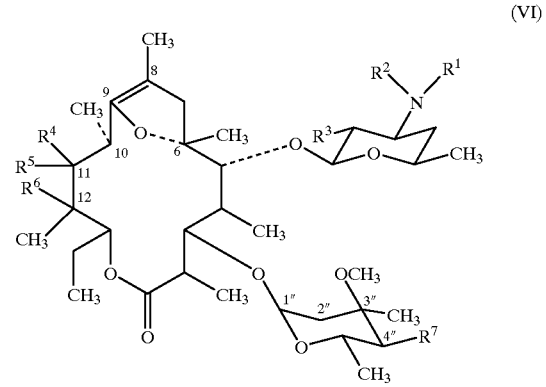

(VI)

wherein $R^1$ and $R^2$, whether identical or not, represent an alkyl having 1 to 6 carbon atoms, an alkenyl having 2 to 6 carbon atoms or an alkynyl having 2 to 6 carbon atoms; $R^3$ represents hydrogen or a hydroxyl group; one of $R^4$ and $R^5$ represents hydrogen and the other represents a hydroxyl group, or $R^4$ and $R^5$ bind together to represent O=; $R^6$ represents hydrogen or a hydroxyl group that may be substituted for; $R^7$ represents hydrogen or a hydroxyl group; or a salt thereof, characterized in that a crude crystal of said 8,9-anhydroerythromycin A-6,9-hemiacetal derivative or a salt thereof is recrystallized as a solvation product from hydrated isopropanol.

9 Claims, No Drawings

METHOD OF PRODUCING ERYTHROMYCIN DERIVATIVE

This application is a continuation of international application number PCT/JP97/00605 filed Feb. 28, 1997

TECHNICAL FIELD

The present invention relates to method of producing an erythromycin derivative or a salt thereof, which is useful as a pharmaceutical for the prevention or treatment of gastrointestinal diseases in mammals, especially those in humans, such as postoperative ileus, diabetic paresis of stomach, maldigestion, reflux esophagitis, pseudoileus, gastrointestinal symptoms accompanying postgastrectomy syndrome (upper abdominal distention, upper abdominal heaviness, nausea, vomiting, heartburn, anorexia, epigastralgia, epigastric tender pain etc.), chronic gastritis, irritable bowel syndrome, and constipation due to morphine or anticancer agent administration.

BACKGROUND ART

As compounds possessing gastrointestinal tract contraction-promoting activity, the erythromycin derivatives, N-demethyl-N-isopropyl-8,9-anhydroerythromycin A-6,9-hemiacetal and N-demethyl-N-ethyl-8,9-anhydroerythromycin A-6,9-hemiacetal are described in Japanese Patent Unexamined Publication Nos. 99092/1988 (EP-A-0215355) and 99016/1988 (EP-A-0215355). These two patent publications disclose a method of producing N-demethyl-N-isopropyl-8,9-anhydroerythromycin A-6,9-hemiacetal by N-isopropylating N-demethyl-8,9-anhydroerythromycin A-6,9-hemiacetal, and a method of producing N-demethyl-N-ethyl-8,9-anhydroerythromycin A-6,9-hemiacetal by treating N-demethyl-N-ethyl-erythromycin A with glacial acetic acid to form a 6,9-hemiacetal ring.

These two patent publications also disclose a method of purifying said desired compounds by silica gel column chromatography.

For N-alkylation reaction of N-demethylerythromycin A, however, alkyl groups having 3 or more carbon atoms (e.g., propyl, isopropyl, butyl, isobutyl etc.), especially branched alkyl groups (e.g., isopropyl, isobutyl etc.), are difficult to introduce, though alkyl groups having 1 to 2 carbon atoms (i.e., methyl, ethyl) are easy to introduce. In addition, yield is low due to the formation of a large amount of byproducts. These are problematic for a process for industrial mass production. The method of producing N-demethyl-N-isopropyl-8,9-anhydroerythromycin A-6,9-hemiacetal described in the above-mentioned Japanese Patent Unexamined Publication Nos. 99092/1988 and 99016/1988 is therefore unpractical as an industrial process.

Also, the method wherein N-demethyl-N-ethyl-erythromycin A is treated under acidic conditions to yield N-demethyl-N-ethyl-8,9-anhydroerythromycin A-6,9-hemiacetal, described in the above-mentioned Japanese Patent Unexamined Publication Nos. 99092/1988 and 99016/1988, is problematic as an industrial process because the starting material N-demethyl-N-ethyl-erythromycin A and the resulting product N-demethyl-N-ethyl-8,9-anhydroerythromycin A-6,9-hemiacetal are both difficult to purify.

Moreover, the method of purifying the desired compound by silica gel column chromatography disclosed in these two patent publications poses some problems, including (i) a lot of time is required to operate such chromatographic treatment and concentrate the eluants after chromatography on an industrial mass scale, and (ii) silica gel is expensive material and difficult to recycle, its use resulting in massive waste. There has therefore been a need for a simple production method of the desired product at high purity and high yield on an industrial mass scale.

DISCLOSURE OF INVENTION

Through extensive investigation of various production methods for erythromycin derivatives, the present inventors found that by reacting N-demethylerythromycin A with an isopropylating agent in the presence of a base and subsequently treating it under acidic conditions, N-demethyl-N-isopropyl-8,9-anhydroerythromycin A-6,9-hemiacetal can be obtained at high yield, with unexpectedly suppressed byproduct formation.

The present inventors also found that by treating N-demethylerythromycin A under acidic conditions and subsequently reacting it with an ethylating agent, N-demethyl-N-ethyl-8,9-anhydroerythromycin A-6,9-hemiacetal can be obtained at high yield.

The present inventors still also found that when the 8,9-anhydroerythromycin A-6,9-hemiacetal derivative represented by the above formula (VI), typically exemplified by N-demethyl-N-isopropyl-8,9-anhydroerythromycin A-6,9-hemiacetal or N-demethyl-N-ethyl-8,9-anhydroerythromycin A-6,9-hemiacetal, is recrystallized from aqueous isopropanol, an isopropanol salvation crystal forms unexpectedly, and a crystal of high purity can be obtained at high yield, with efficient removal of impurities. This isopropanol salvation crystallization method has for the first time made it possible to produce the desired compound without silica gel column chromatography separation, a process very problematic for industrial production due to difficulty in mass treatment.

The present inventors made further investigation based on these findings, and developed the present invention.

The present invention provides a method of producing erythromycin derivatives, especially N-demethyl-N-isopropyl-8,9-anhydroerythromycin A-6,9-hemiacetal and N-demethyl-N-ethyl-8,9-anhydroerythromycin A-6,9-hemiacetal, at high yield and high quality suitable for industrial mass production.

Accordingly, the present invention relates to:

(1) a method of producing the N-demethyl-N-isopropylerythromycin A represented by formula (II):

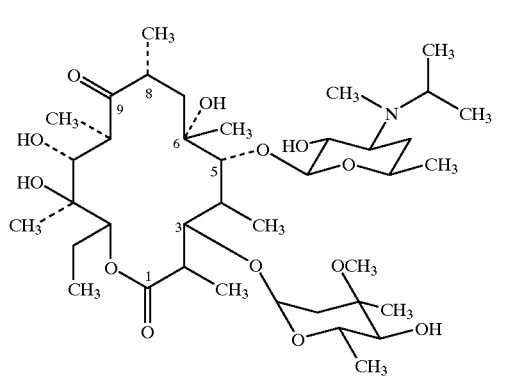

or a salt thereof, characterized in that the N-demethylerythromycin A represented by formula (I):

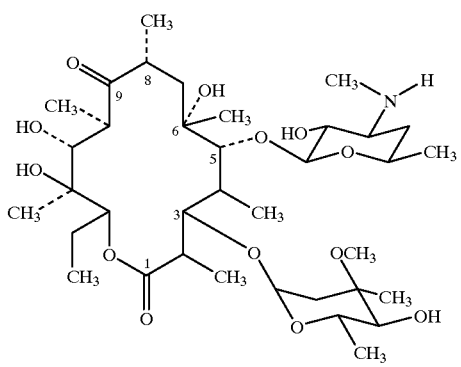

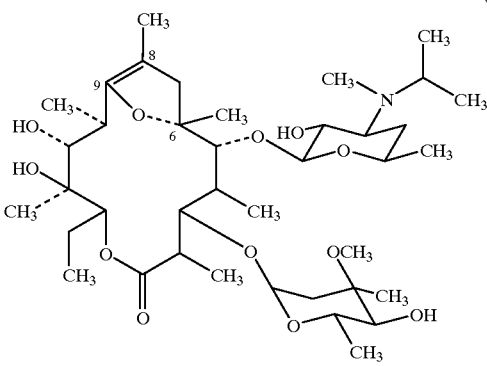

or a salt thereof, is reacted with an isopropylating agent, (2) a method of producing the N-demethyl-N-isopropyl-8, 9-anhydroerythromycin A-6,9-hemiacetal represented by formula (III):

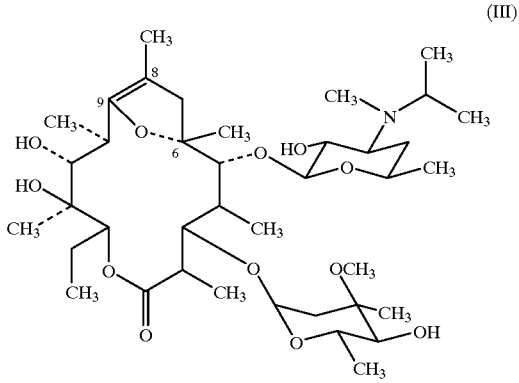

or a salt thereof, characterized in that the N-demethyl-N-isopropylerythromycin A represented by formula (II):

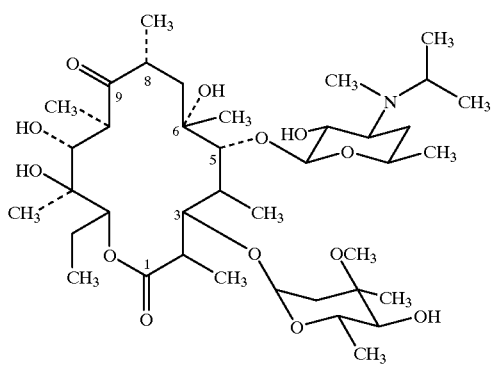

or a salt thereof, is treated under acidic conditions, (3) a method of producing the N-demethyl-N-isopropyl-8, 9-anhydroerythromycin A-6,9-hemiacetal represented by formula (III);

or a salt thereof, characterized in that the N-demethylerythromycin A represented by formula (I):

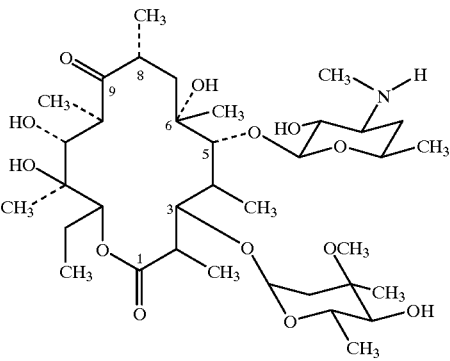

or a salt thereof, is reacted with an isopropylating agent and subsequently treated under acidic conditions, (4) a method of producing the N-demethyl-8,9-anhydroerythromycin A-6,9-hemiacetal represented by formula (IV):

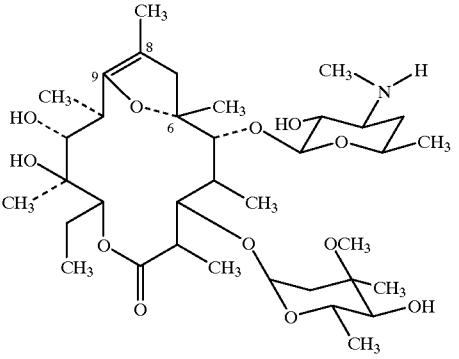

or a salt thereof, characterized in that the N-demethylerythromycin A represented by formula (I):

(I)

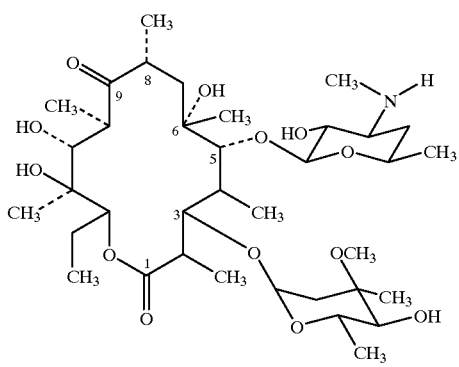

or a salt thereof, is treated under acidic conditions, (5) a method of producing the N-demethyl-N-ethyl-8,9-anhydroerythromycin A-6,9-hemiacetal represented by formula (V):

(V)

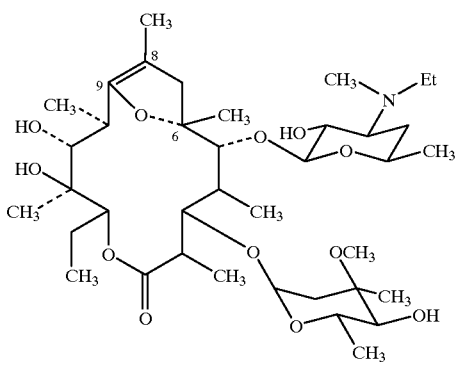

or a salt thereof, characterized in that the N-demethyl-8,9-anhydroerythromycin A-6,9-hemiacetal represented by formula (IV):

(IV)

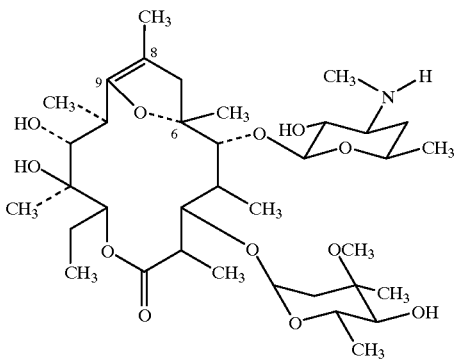

is reacted with an ethylating agent, (6) a method of producing the N-demethyl-N-ethyl-8,9-anhydroerythromycin A-6,9-hemiacetal represented by formula (V):

(V)

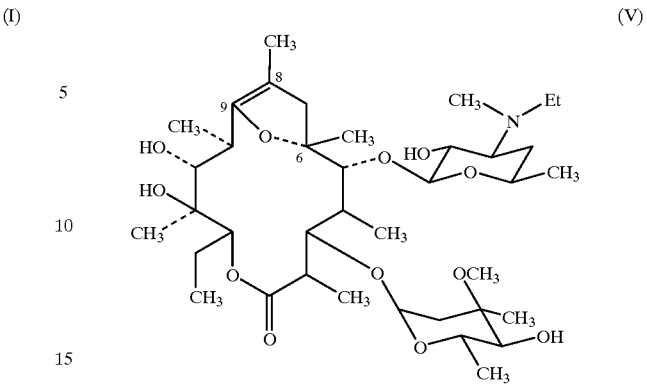

or a salt thereof, characterized in that the N-demethylerythromycin A represented by formula (I):

(I)

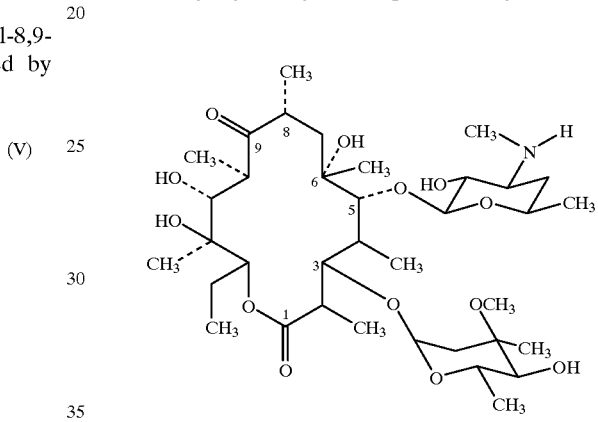

or a salt thereof, is treated under acidic conditions and subsequently reacted with an ethylating agent, and (7) a method of producing a substantially pure crystal of an 8,9-anhydroerythromycin A-6,9-hemiacetal derivative represented by formula (VI):

(VI)

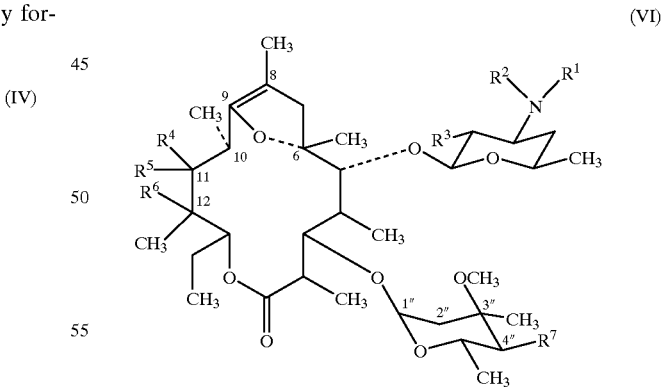

wherein $R^1$ and $R^2$, whether identical or not, represent an alkyl having 1 to 6 carbon atoms, an alkenyl having 2 to 6 carbon atoms or an alkynyl having 2 to 6 carbon atoms; $R^3$ represents hydrogen or a hydroxyl group; one of $R^4$ and $R^5$ represents hydrogen and the other represents a hydroxyl group, or $R^4$ and $R^5$ bind together to represent O═; $R^6$ represents hydrogen or a hydroxyl group that may be substituted for; $R^7$ represents hydrogen or a hydroxyl group; or a salt thereof, characterized in that a crude crystal of said 8,9-anhydroerythromycin A-6,9-hemiacetal derivative or a salt thereof is recrystallized as a solvated product from aqueous isopropanol.

BEST MODE FOR CARRYING OUT THE INVENTION

The formulas above and the various definitions encompassed in the scope of the present invention are hereinafter described with reference to preferable examples thereof.

In the method of the present invention, N-demethyl-N-isopropyl-8,9-anhydroerythromycin A-6,9-hemiacetal can be produced by, for example, reacting N-demethylerythromycin A (described in Japanese Patent Unexamined Publication No. 9129/1972) as a starting compound with a halogen compound in the presence of a base and subsequently treating it under acidic conditions.

Also, N-demethyl-N-ethyl-8,9-anhydroerythromycin A-6,9-hemiacetal can be produced by, for example, treating N-demethylerythromycin A (described above) as a starting compound under acidic conditions and subsequently reacting it with a halogen compound in the presence of a base.

Said halogen compound is exemplified by halogenated $C_{1-6}$ alkyls resulting from binding of an alkyl having 1 to 6 carbon atoms (e.g., methyl, ethyl, propyl, hexyl etc.) and a halogen, halogenated $C_{2-6}$ alkenyls resulting from binding of an alkenyl having 2 to 6 carbon atoms (e.g., vinyl, 1-propenyl, allyl, hexenyl etc.) and a halogen, and halogenated $C_{2-6}$ alkynyls resulting from binding of an alkynyl having 2 to 6 carbon atoms (e.g., ethynyl, 1-propynyl, 2-propynyl, hexynyl etc.) and a halogen. Preferable examples of said halogen compound include isopropyl halides in the case of N-demethyl-N-isopropyl-8,9-anhydroerythromycin A-6,9-hemiacetal, and ethyl halides in the case of N-demethyl-N-ethyl-8,9-anhydroerythromycin A-6,9-hemiacetal. The halogen in said halogen compound is exemplified by chlorine, bromine and iodine, with preference given to iodine.

More specifically, said halogen compound is exemplified by methyl iodide, ethyl iodide, propyl iodide, isopropyl iodide, propenyl iodide, ethynyl iodide and propynyl iodide, with preference given to methyl iodide, ethyl iodide, propyl iodide and isopropyl iodide.

The amount of halogen compound used in said reaction is about 1 to 100 mol equivalents, preferably 2 to 25 mol equivalents, per mol of the starting compound N-demethylerythromycin A (or bis-configuration thereof).

Usable solvents for said reaction include halogenated hydrocarbons (e.g., chloroform, dichloromethane etc.), ethers (e.g., ethyl ether, tetrahydrofuran etc.), ketones (e.g., acetone, methyl ethyl ketone), esters (e.g., ethyl acetate etc.), alcohols (e.g., methanol, ethanol etc.), nitrites (e.g., acetonitrile etc.) and amides (e.g., N,N-dimethylformamide, N,N-dimethylamide etc.), with preference given to nitriles and ketones, particularly acetonitrile.

Useful bases for said reaction include tertiary amines (e.g., triethylamine, tri-n-propylamine etc.), metal carbonates (e.g., potassium carbonate, sodium carbonate, lithium carbonate etc.) and metal hydrogen carbonates (e.g., sodium hydrogen carbonate, potassium hydrogen carbonate etc.), with preference given to sodium carbonate and triethylamine.

Said reaction is normally carried out at ice cooling temperature (about 0° C.) to solvent boiling point (about 100° C.), preferably at room temperature (about 15 to 25° C.) to about 80° C.

Useful acids for the treatment under acidic conditions include, for example, organic acids (formic acid, acetic acid, propionic acid, oxalic acid, fumaric acid, maleic acid etc.) and mineral acids (sulfuric acid, phosphoric acid etc.), particularly acetic acid. These acids may be applied to be diluted with halogenated hydrocarbons, ethers, ketones etc. as appropriate.

The amount of acid used is about 1 to 200 mol equivalents, preferably 30 to 100 mol equivalents, per mol of N-demethylerythromycin A.

Said reaction is carried out at ice cooling temperature (about 0° C.) to solvent boiling point (about 100° C.), preferably at room temperature (about 15 to 25° C.) to about 80° C.

The desired compound obtained, i.e., an N-demethyl-N-alkyl-, N-demethyl-N-alkenyl- or N-demethyl-N-alkynyl-8,9-anhydroerythromycin A-6,9-hemiacetal, can be purified by isolating it by commonly known means such as concentration, liquid nature conversion, extraction, solvent extraction and crystallization, and subsequently treating it by recrystallization, chromatography etc.

The present invention is characterized by recrystallizing as an isopropanol solvation product a crude crystal of a compound represented by formula (VI) above, which contains the desired compound obtained according to the method descried above, i.e., an N-demethyl-N-alkyl-, N-demethyl-N-alkenyl- or N-demethyl-N-alkynyl-8,9-anhydroerythromycin A-6,9-hemiacetal, from aqueous isopropanol, i.e., an isopropanol/water mixed solvent. Subsequent recrystallization from a mixed solvent such as acetonitrile/water makes it possible to yield the desired compound represented by formula (VI) as a substantially pure crystal at high yield.

With respect to formula (VI) above, $R^1$ and $R^2$, whether identical or not, represent an alkyl having 1 to 6 carbon atoms (e.g., methyl, ethyl, propyl, isopropyl, hexyl etc.), an alkenyl having 2 to 6 carbon atoms (e.g., vinyl, 1-propenyl, allyl, hexenyl etc.) or an alkynyl having 2 to 6 carbon atoms (e.g., ethynyl, 1-propynyl, 2-propynyl, hexynyl etc.), preferably an alkyl having 1 to 4 carbon atoms, more preferably ethyl or isopropyl.

$R^3$ represents hydrogen or a hydroxyl group.

One of $R^4$ and $R^5$ represents hydrogen and the other represents a hydroxyl group, or $R^4$ and $R^5$ bind together to represent O=, with preference given to the case wherein one is hydrogen atom and the other is a hydroxyl group.

$R^6$ represents hydrogen or a hydroxyl group that may be substituted for. In this case, the hydroxyl group that may be substituted for represents a hydroxyl group or a hydroxyl group substituted for by an alkyl having 1 to 6 carbon atoms (e.g., methyl, ethyl, propyl, isopropyl, hexyl etc.), an alkenyl having 2 to 6 carbon atoms (e.g., vinyl, 1-propenyl, allyl, hexenyl etc.) or an alkynyl having 2 to 6 carbon atoms (e.g., ethynyl, 1-propynyl, 2-propynyl, hexynyl etc.), preferably a hydroxyl group or a hydroxyl group substituted for by an alkyl having 1 to 4 carbon atoms, more preferably a hydroxyl group.

$R^7$ represents hydrogen or a hydroxyl group, preferably a hydroxyl group.

In the present invention, the compound represented by formula (VI) above is exemplified by N-demethyl-N-isopropyl-8,9-anhydroerythromycin A-6,9-hemiacetal, N-demethyl-N-ethyl-8,9-anhydroerythromycin A-6,9-hemiacetal, 12-dehydroxy-4"-dehydroxy-N-demethyl-N-isopropyl-8,9-anhydroerythromycin A-6,9-hemiacetal, N-demethyl-N-isopropyl-12-methoxy-8,9-anhydroerythromycin A-6,9-hemiacetal and N-demethyl-N-isopropyl-12-methoxy-11-oxo-8,9-anhydroerythromycin A-6,9-hemiacetal, with preference given to N-demethyl-N-isopropyl-8,9-anhydroerythromycin A-6,9-hemiacetal.

The isopropanol for recrystallization is used in a volume about 1 to 20 times, preferably 2 to 5 times, that of the substrate, whereas water is used in a volume about 1 to 20 times, preferably 2 to 10 times, that of the substrate. The ratio of isopropanol and water is about 1:0.5 to 1:3, preferably 1:1 to 1:2.

The desired compound obtained may form a salt upon acid treatment. Said acid is exemplified by organic acids (e.g., glycoheptonic acid, stearic acid, propionic acid, lactobionic acid, oxalic acid, maleic acid, fumaric acid, succinic acid, lactic acid, trifluoroacetic acid, acetic acid, methanesulfonic acid, p-toluenesulfonic acid, benzenesulfonic acid etc.) and mineral acids (e.g., sulfuric acid, hydrochloric acid, hydroiodic acid, phosphoric acid, nitric acid etc.).

The salt of the desired compound of the present invention is preferably a pharmaceutically acceptable salt, exemplified by salts with inorganic acids, salts with organic acids, and salts with basic or acidic amino acids. Preferable salts with inorganic acids include, for example, salts with hydrochloric acid, hydrobromic acid, nitric acid, sulfuric acid, phosphoric acid etc. Preferable salts with organic acids include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc. Preferable salts with basic amino acids include, for example, salts with arginine, lysine, ornithine etc. Preferable salts with acidic amino acids include, for example, salts with aspartic acid, glutamic acid etc.

The desired compound of the present invention can be administered orally or non-orally, as formulated with a pharmaceutically acceptable carrier, in the form of solid preparations such as tablets, capsules, granules and powders, or liquid preparations such as syrups and injectable preparations.

Pharmaceutically acceptable carriers are various organic or inorganic carrier substances in common use as pharmaceutical materials, including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary.

Preferable excipients include, for example, lactose, sucrose, D-mannitol, starch, crystalline cellulose and light silicic anhydride.

Preferable lubricants include, for example, magnesium stearate, calcium stearate, talc and colloidal silica.

Preferable binders include, for example, binding cellulose, sucrose, D-mannitol, trehalose, dextrin, hydroxypropyl cellulose, hydroxypropylmethyl cellulose and polyvinylpyrrolidone.

Preferable disintegrants include, for example, starch, carboxymethyl cellulose, carboxymethyl cellulose calcium, croscarmellose sodium and carboxymethyl starch sodium.

Preferable solvents include, for example, water for injection, alcohol, propylene glycol, macrogol, sesame oil, corn oil and tricaprylin.

Preferable dissolution aids include, for example, polyethylene glycol, propylene glycol, D-mannitol, trehalose, benzyl benzoate, ethanol, tris-aminomethane, cholesterol, triethanolamine, sodium carbonate and sodium citrate.

Preferable suspending agents include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Preferable isotonizing agents include, for example, sodium chloride, glycerol and D-mannitol.

Preferable buffers include, for example, buffer solutions of phosphates, acetates, carbonates, citrates etc.

Preferable soothing agents include, for example, benzyl alcohol.

Preferable preservatives include, for example, p-oxybenzoic acid esters, chlorobutanol, benzyl alcohol, phenethyl alcohol, dehydroacetic acid and sorbic acid.

Preferable antioxidants include, for example, sulfites and ascorbic acid.

Preparations of the erythromycin derivatives obtained by the present invention, e.g., N-demethyl-N-isopropyl-8,9-anhydroerythromycin A-6,9-hemiacetal, N-demethyl-N-ethyl- 8,9-anhydroerythromycin A-6,9-hemiacetal, 12-dehydroxy-4"-dehydroxy-N-demethyl-N-isopropyl-8,9-anhydroerythromycin A-6,9-hemiacetal, N-demethyl-N-isopropyl-12-methoxy-8,9-anhydroerythromycin A-6,9-hemiacetal and N-demethyl-N-isopropyl-12-methoxy-11-oxo-8,9-anhydroerythromycin A-6,9-hemiacetal, or salts thereof, are specifically exemplified by those shown in the following reference examples.

The erythromycin derivatives of the present invention, more specifically N-demethyl-N-isopropyl-8,9-anhydroerythromycin A-6,9-hemiacetal and N-demethyl-N-ethyl-8,9-anhydroerythromycin A-6,9-hemiacetal, for example, are of low toxicity and can be used as pharmaceuticals for the prevention or treatment of gastrointestinal diseases in mammals (e.g., humans, horses, bovines, swines, dogs, cats, mice, rats etc.), especially those in humans, such as postoperative ileus, diabetic paresis of stomach, maldigestion, reflux esophagitis, pseudoileus, gastrointestinal symptoms accompanying postgastrectomy syndrome (e.g., upper abdominal distention, upper abdominal heaviness, nausea, vomiting, heartburn, anorexia, epigastralgia, epigastric tender pain), chronic gastritis, irritable bowel syndrome, and constipation due to morphine or anticancer agent administration.

Although the doses of N-demethyl-N-isopropyl-8,9-anhydroerythromycin A-6,9-hemiacetal and N-demethyl-N-ethyl-8,9-anhydroerythromycin A-6,9-hemiacetal, compounds both encompassed in the scope of the present invention, are variable according to the route of administration and symptoms of the patient to be treated, they can be chosen over the range from about 0.1 to 500 mg/kg, preferably from 1.0 to 100 mg/kg, for oral administration, or from about 0.01 to 100 mg/kg, preferably from 0.1 to 10 mg/kg, for non-oral administration (e.g., administration by intravenous injection), both for each adult per day.

The present invention is hereinafter described in more detail by means of, but not limited to, the following reference examples and working examples.

REFERENCE EXAMPLE 1

Production of N-demethylerythromycin A 23.0 kg of erythromycin A (Upjohn, USA) was dissolved in 196 L of methanol; a solution of 21.6 kg of sodium acetate trihydrate in 46 L of water was added, followed by heating to 50° C. and addition of 8.1 kg of iodine under stirring conditions. To maintain pH 8 to 9, 35 L of 1 N NaOH was added 10 minutes later, 19 L of 1 N NaOH 30 minutes later, 4.1 kg of iodine and 7.4 L of 1 N NaOH 60 minutes later, 9.9 L of 1 N NaOH 75 minutes later, 2.1 kg of iodine and 7.4 L of 1 N NaOH 105 minutes later, and 12 L of 1 N NaOH 135 minutes later. The reaction was continued at 50° C. under stirring conditions for 1 more hour. The reaction product was cooled; a solution containing 5.8 kg of sodium thiosulfate, 17.5 L of concentrated aqueous ammonia and 175 L of water was added, followed by 2 times of extraction with 115 L of methylene chloride. After the methylene chloride solution was washed with 44 L of dilute aqueous ammonia containing 9 L of concentrated aqueous ammonia, the solvent was distilled off under reduced pressure. After the residue obtained was dissolved by the addition of 35 L of acetone, 35 L of isopropyl ether and 5 L of concentrated aqueous ammonia were added for crystallization to give 16.9 kg (yield 74.9%) of a white crystal of N-demethylerythromycin A.

REFERENCE EXAMPLE 2

Production of N-demethylerythromycin A 150.0 g of erythromycin A (same as above) was dissolved in 1,680 ml of methanol; a solution of 142.0 g of sodium acetate trihydrate in 600 ml of water was added. While the reaction mixture was kept at pH 8.5 and a temperature of 50° C. by adding 1 N NaOH as appropriate, a solution of 62.0 g of iodine in 1,500 ml of methanol was added over a period of 2 hours. After the reaction was continued at 50° C. under stirring conditions for 1 more hour, it was treated in the same manner as in Reference Example 1 to give 132.0 g (yield 90%) of a white crystal of N-demethylerythromycin A.

REFERENCE EXAMPLE 3

Production of N-demethylerythromycin A

After 10.0 g of N-demethylerythromycin A obtained in Reference Example 2 was dissolved in 15 ml of methanol at room temperature, it was crystallized by adding 25 ml of water to yield 9.02 g (yield 90%) of N-demethylerythromycin A.

EXAMPLE 1

Production of N-demethyl-N-isopropyl-8,9-anhydroerythromycin A-6,9-hemiacetal

To 16.9 kg of N-demethylerythromycin A obtained in Reference Example 1, 20.0 kg of 2-iodopropane, 5.9 kg of triethylamine and 42 L of acetonitrile were added, followed by stirring at 60 to 65° C. for 24 hours to cause the reaction. After stirring, the solvent was distilled off from the reaction product under reduced pressure to yield N-demethyl-N-isopropylerythromycin A.

To this N-demethyl-N-isopropylerythromycin A, 71 L of glacial acetic acid and 141 L of methylene chloride were added, followed by stirring at room temperature for 1 hour to cause the reaction. The reaction product was poured over 327 L of cold water containing 141 L of aqueous ammonia and extracted twice with 71 L of dichloromethane. The dichloromethane solution was washed with 142 L of water and dried with anhydrous sodium sulfate, after which it was filtered; the solvent was distilled off from the filtrate under reduced pressure. The residue obtained was dissolved in 14 L of acetonitrile and crystallized by adding 14 L of water to give 14.0 kg (yield 80%) of a white crystal of N-demethyl-N-isopropyl-8,9-anhydroerythromycin A-6,9-hemiacetal.

EXAMPLE 2

Production of N-demethyl-N-isopropyl-8,9-anhydroerythromycin A-6,9-hemiacetal

To 30.0 g of N-demethylerythromycin A obtained in Reference Example 3, 35.4 g of 2-iodopropane, 30.0 g of anhydrous sodium carbonate and 150 ml of acetonitrile were added, followed by stirring at 73 to 78° C. for 8 hours to cause the reaction. After stirring, the solvent was distilled off from the reaction product under reduced pressure; and then 300 ml of dichloromethane and 300 ml of water were then added to the residue, followed by stirring to dissolve the residue. The dichloromethane layer was collected; the aqueous layer was further extracted with 100 ml of dichloromethane, and then the dichloromethane layers were combined. The dichloromethane solution obtained was washed with 200 ml of water and dried with anhydrous sodium sulfate, after which it was filtered; the solvent was distilled off from the filtrate under reduced pressure to yield N-demethyl-N-isopropylerythromycin A.

To this N-demethyl-N-isopropylerythromycin A, 150 ml of glacial acetic acid and 75 ml of dichloromethane were added, followed by stirring at room temperature for 1 hour to cause the reaction. The reaction product was poured over 720 ml of cold water containing 240 ml of aqueous ammonia and extracted twice with 240 ml of dichloromethane. The dichloromethane solution was washed with 240 ml of water and dried with anhydrous sodium sulfate, after which it was filtered; the solvent was distilled off from the filtrate under reduced pressure. The residue obtained was dissolved in 130 ml of acetonitrile and crystallized by adding 130 ml of water to give 25.0 g (yield 80.6%) of N-demethyl-N-isopropyl-8,9-anhydroerythromycin A-6,9-hemiacetal.

EXAMPLE 3

Production of N-demethyl-N-isopropyl-8,9-anhydroerythromycin A-6,9-hemiacetal

To 5.00 g of N-demethyl-N-isopropyl-8,9-anhydroerythromycin A-6,9-hemiacetal obtained in Example 2, 12.5 ml of isopropanol was added, followed by dissolution under heating conditions, after which 15 ml of water was added in 3 portions for crystallization to give 4.90 g (yield 90%) of N-demethyl-N-isopropyl-8,9-anhydroerythromycin A-6,9-hemiacetal isopropanol monosolvate. This 4.90 g of solvate was recrystallized from a mixture of acetonitrile and water to give 4.11 g (yield 82%) of purified N-demethyl-N-isopropyl-8,9-anhydroerythromycin A-6,9-hemiacetal.

EXAMPLE 4

Production of N-demethyl-8,9-anhydroerythromycin A-6,9-hemiacetal

To 5.00 g of N-demethylerythromycin A obtained in Reference Example 1, 20 ml of glacial acetic acid was added, followed by stirring at room temperature for 1 hour to cause the reaction. The reaction product was poured over 120 ml of cold water containing 40 ml of aqueous ammonia and extracted twice with 40 ml of dichloromethane. The dichloromethane solution was washed with 40 ml of water and dried with anhydrous sodium sulfate, after which it was filtered; the solvent was distilled off from the filtrate under reduced pressure. The residue obtained was dissolved in 25 ml of ethyl acetate under heating conditions, after which it was cooled for crystallization to give 4.14 g (yield 85%) of a white crystal of N-demethyl-8,9-anhydroerythromycin A-6,9-hemiacetal.

EXAMPLE 5

Production of N-demethyl-N-ethyl-8,9-anhydroerythromycin A-6,9-hemiacetal

To 5.50 kg of N-demethyl-8,9-anhydroerythromycin A-6,9-hemiacetal obtained in Example 4, 16.7 kg of iodoethane, 3.60 kg of triethylamine and 25 L of methanol were added, followed by stirring at 50 to 55° C. for 2.5 hours to cause the reaction. The solvent was distilled off from the reaction product under reduced pressure; the residue obtained was dissolved by adding 50 L of dichloromethane and 100 L of water. The dichloromethane layer was collected; the aqueous layer was further extracted with 50 L of dichloromethane, after which the dichloromethane layers were combined. The dichloromethane solution obtained was washed with 50 L of aqueous saturated sodium hydrogen carbonate solution and dried with anhydrous sodium sulfate, after which it was filtered; the solvent was distilled off from the filtrate under reduced pressure. The residue obtained was dissolved in 20 L of acetone and crystallized by adding 25 L of water to give 3.81 kg (yield 74%) of a white crystal of N-demethyl-N-ethyl-8,9-anhydroerythromycin A-6,9-hemiacetal.

REFERENCE EXAMPLE 4

Production of N-demethyl-N-isopropyl-8,9-anhydroerythromycin A-6,9-hemiacetal

To 5.00 g of N-demethyl-8,9-anhydroerythromycin A-6,9-hemiacetal obtained in Example 4, 12.1 g of 2-iodopropane, 7.2 g of triethylamine and 35 ml of N,N-dimethylformamide were added, followed by stirring at 50 to 55° C. for 34 hours to cause the reaction. The reaction product was added to 100 ml of water and extracted twice with 50 ml of dichloromethane. The dichloromethane solution was washed with 50 ml of water and dried with anhydrous sodium sulfate, after which it was filtered; the solvent was distilled off from the filtrate under reduced pressure. The residue obtained was purified by silica gel chromatography [developing solvent, dichloromethane/methanol (10:1)], after which it was crystallized in a mixture of acetonitrile and water to give 1.78 g (yield 33%) of a white crystal of N-demethyl-N-isopropyl-8,9-anhydroerythromycin A-6,9-hemiacetal.

REFERENCE EXAMPLE 5

Production of N-demethyl-N-isopropyl-8,9-anhydroerythromycin A-6,9-hemiacetal 9.37 kg of N-demethyl-N-isopropyl-8,9-anhydroerythromycin A-6,9-hemiacetal obtained in Example 1 was recrystallized from a mixture of 3.7 L of isopropyl ether and 19 L of n-hexane. The crystal obtained was purified by silica gel chromatography [developing solvent, dichloromethane/methanol=10:1]; the effective fractions were collected and the solvent was distilled off under reduced pressure. The residue obtained was dissolved in 42 L of acetonitrile and crystallized by adding 42 L of water to give 6.78 kg (yield 72%) of purified N-demethyl-N-isopropyl-8,9-anhydroerythromycin A-6,9-hemiacetal.

REFERENCE EXAMPLE 6

Production of N-demethyl-N-ethyl-8,9-anhydroerythromycin A-6,9-hemiacetal

To 5.00 g of N-demethylerythromycin A obtained in Reference Example 1, 16.25 g of iodoethane, 3.15 g of triethylamine and 25 ml of methanol were added, followed by stirring at 50 to 55° C. for 2.5 hours to cause the reaction. The solvent was distilled off from the reaction product under reduced pressure to yield N-demethyl-N-ethyl-erythromycin A.

To this N-demethyl-N-ethyl-erythromycin A, 20 ml of glacial acetic acid was added, followed by stirring at room temperature for 1 hour to cause the reaction. The reaction product was poured over 120 ml of cold water containing 40 ml of aqueous ammonia and extracted twice with 40 ml of dichloromethane. The dichloromethane solution was washed with 40 ml of water and dried with anhydrous sodium sulfate, after which it was filtered; the solvent was distilled off from the filtrate under reduced pressure. The residue obtained was dissolved in 20 ml of acetone and crystallized by adding 40 ml of water to give 3.95 g (yield 78%) of a white crystal of N-demethyl-N-ethyl-8,9-anhydroerythromycin A-6,9-hemiacetal.

REFERENCE EXAMPLE 7

Production of N-demethyl-N-isopropyl-8,9-anhydroerythromycin A-6,9-hemiacetal 1.00 g of N-demethylerythromycin A obtained in Reference Example 1 was treated with glacial acetic acid in the same manner as in Reference Example 3, after which it was treated in the same manner as in Reference Example 1, using 1.18 g of l-iodopropane, 0.35 g of triethylamine and 2.5 ml of acetonitrile, to give 1.01 g (yield 73%) of a white crystal of N-demethyl-N-isopropyl-8,9-anhydroerythromycin A-6,9-hemiacetal.

REFERENCE EXAMPLE 8

Production of Capsular Preparation

As shown in Table 1, 25 g of component 1), 539 g of component 2), 360 g of component 3), 120 g of component 4), 60 g of component 5) and 60 g of component 6) were mixed in a vertical granulator (produced by Powrex Corporation, Japan), after which they were kneaded with separately added 556 g of an aqueous solution of 60 g of component 7) and 12 g of component 8).

This kneaded product was extruded at a screen size of 0.8 mm diameter using DOME GRAN (produced by Fuji Paudal Co., Ltd., Japan); the resulting granular product was made spherical using the Marumerizer (produced by Fuji Paudal Co., Ltd.), after which it was dried using a fluidized granulator drier (produced by Powrex Corporation) to yield principal agent granules of N-demethyl-N-isopropyl-8,9-anhydroerythromycin A-6,9-hemiacetal (hereinafter referred to as compound A).

840 g of the principal agent granules of N-demethyl-N-isopropyl-8,9-anhydroerythromycin A-6,9-hemiacetal (compound A) was placed in a fluidized granulator drier (produced by Powrex Corporation) and coated with 938 g of an aqueous solution containing 46.9 g of component 9) to yield sub-coated granules.

760.2 g of the sub-coated granules was placed in the same machine and further coated with 1,894.2 g of a suspension containing 586.2 g of component 10) (175.8 g as solid content), 52.8 g of component 11), 17.4 g of component 12) and 7.8 g of component 13) to yield enteric granules.

845 g of these enteric granules, 2.5 g of component 14) and 2.5 g of component 15) were mixed using a tumbler mixer (produced by Showa Kagaku Kikai Kosakusho, Japan) to yield mixed granules. 765 g of these mixed granules was treated using a capsule filling machine (produced by Zanasi Co.) to yield a No. 3 capsular preparation.

A 5.0 mg capsular preparation was produced in the same manner as above.

TABLE 1

(Compound A: N-demethyl-N-isopropyl-8,9-anhydroerythromycin A-6,9-hemiacetal)

| Composition | 2.5 mg Capsule | 5 mg Capsule |
|---|---|---|
| [Principal agent granules] | | |
| 1) Compound A | 2.5mg | 5.0mg |
| 2) Lactose | 53.9 | 51.4 |
| 3) Corn starch | 36.0 | 36.0 |
| 4) Crystalline cellulose | 12.0 | 12.0 |
| 5) Croscarmellose sodium | 6.0 | 6.0 |
| 6) Hydroxypropyl cellulose | 6.0 | 6.0 |
| 7) Macrogol 6000 | 2.4 | 2.4 |
| 8) Polysorbate 80 | 1.2 | 1.2 |
| Subtotal | 120.0mg | 120.0mg |
| [Sub-coated granules] | | |
| Principal agent granules | 120.0mg | 120.0mg |
| 9) Hydroxypropylmethyl cellulose 2910 | 6.7 | 6.7 |
| Subtotal | 126.7mg | 126.7mg |
| [Enteric granules] | | |
| Sub-coated granules | 126.7mg | 126.7mg |
| 10) Methacrylic acid copolymer LD (Eudragit L30D-55$^R$) | 29.3 | 29.3 |
| 11) Talc | 8.8 | 8.8 |
| 12) Macrogol 6000 | 2.9 | 2.9 |
| 13) Polysorbate 80 | 1.3 | 1.3 |
| | 169.0mg | 169.0mg |
| [Mixed granules] | | |
| Enteric granules | 169.0mg | 169.0mg |
| 14) Talc | 0.5 | 0.5 |
| 15) Light silicic anhydride | 0.5 | 0.5 |
| | 170.0mg | 170.0mg |
| [Capsular preparation] | | |
| Mixed granules | 170.0mg | 170.0mg |
| 16) Gelatin capsule (No. 3) | 51.0 | 51.0 |
| | 221.0mg | 221.0mg |

The acid resistance in solution 1, dissolution in solution 2, and other preparation properties of the capsular preparation obtained were good.

REFERENCE EXAMPLE 9

Production of Capsular Preparation

Capsule A, having the composition per capsule shown in Table 2, was produced as described below. First, 87.5 g of component 1), 542.5 g of component 3), 490 g of component 4) and 350 g of component 5) were thoroughly mixed to yield a dusting powder. 2,730 g of component 2) was placed in a centrifugal fluidized coating granulator (produced by Freund Industrial Co., Ltd., CF-3600) and coated with the above dusting powder, while 1,120 g of an aqueous solution of 28 g of component 6) was sprayed.

Further, 143.5 g of component 3), 161 g of component 4) and 157.5 g of component 5) were thoroughly mixed to yield a secondary dusting powder, which was then used for coating subsequent to coating with the above dusting powder to yield spherical granules.

These spherical granules were vacuum dried at 40° C. for 16 hours and sieved through a round sieve to yield 710 to 1,000$\mu$ principal agent granules.

4,020 g of said principal agent granules was placed in a fluidized granulator drier (produced by Powrex Corporation) and coated with 4,020 g of an aqueous solution containing 201 g of component 7) to yield sub-coated granules.

3,940 g of the sub-coated granules was placed in the same machine and further coated with 8,838.7 g of a suspension containing 820.4 g of component 8) (2,734.7 g as 30% methacrylic acid copolymer emulsion), 246.4 g of component 9), 81.2 g of component 10) and 36.4 g of component 11) to yield enteric granules.

4,501.8 g of these enteric granules, 12.3 g of component 12) and 12.3 g of component 13) were mixed using a tumbler mixer (produced by Showa Kagaku Kikai Kosakusho) to yield mixed granules, 4,379.2 g of which was filled in No. 3 gelatin capsules using a capsule filling machine (produced by Zanasi Co.) to yield capsule A.

REFERENCE EXAMPLE 10

In the same manner as in Reference Example 9, capsules B and C, having the respective compositions per capsule shown in Table 2, were produced.

REFERENCE EXAMPLE 11

Using the mixed granules obtained when capsule C was produced in Reference Example 10, and No. 1 gelatin capsules, capsule D, containing 20 mg of compound A per capsule, was obtained.

TABLE 2

(Compound A: N-demethyl-N-isopropyl-8,9-anhydroerythromycin A-6,9-hemiacetal)

| Composition (per capsule) | Capsule A | Capsule B | Capsule C |
|---|---|---|---|
| [Principal agent granules] | | | |
| 1) Compound A | 2.5mg | 5.0mg | 10.0mg |
| 2) Sucrose-starch spherical granules | 78.0 | 78.0 | 78.0 |
| 3) Purified sucrose | 19.6 | 19.1 | 16.1 |
| 4) Corn starch | 18.6 | 16.6 | 14.6 |
| 5) Low substitutional hydroxypropyl cellulose | 14.5 | 14.5 | 14.5 |
| 6) Hydroxypropyl cellulose | 0.8 | 0.8 | 0.8 |
| Subtotal | 134.0 | 134.0 | 134.0 |
| [Sub-coated granules] | | | |
| Principal agent granules | 134.0 | 134.0 | 134.0 |
| 7) Hydroxypropylmethyl cellulose 2910 | 6.7 | 6.7 | 6.7 |
| Subtotal | 140.7 | 140.7 | 140.7 |
| [Enteric granules] | | | |
| Sub-coated granules | 140.7 | 140.7 | 140.7 |

TABLE 2-continued (Compound A: N-demethyl-N-isopropyl-8,9-anhydroerythromycin A-6,9-hemiacetal)

| Composition (per capsule) | Capsule A | Capsule B | Capsule C |
|---|---|---|---|
| 8) Methacrylic acid copolymer LD | 29.3 | 29.3 | 29.3 |
| 9) Talc | 8.8 | 8.8 | 8.8 |
| 10) Macrogol 6000 | 2.9 | 2.9 | 2.9 |
| 11) Polysorbate 80 | 1.3 | 1.3 | 1.3 |
| Subtotal [Mixed granules] | 183.0 | 183.0 | 183.0 |
| Enteric granules | 180.3 | 183.0 | 183.0 |
| 12) Talc | 0.5 | 0.5 | 0.5 |
| 13) Light silicic anhydride | 0.5 | 0.5 | 0.5 |
| Subtotal [Capsular preparation] | 184.0 | 184.0 | 184.0 |
| Mixed granules | 184.0 | 184.0 | 184.0 |
| 14) No. 3 gelatin capsule | 50.0 | 50.0 | 50.0 |
| Total | 234.0 | 234.0 | 234.0 |

The acid resistance in solution 1, dissolution in solution 2, and other preparation properties of the capsular preparations obtained were good.

REFERENCE EXAMPLE 12

Production of Capsular Preparation

Capsule E, having the composition per capsule shown in Table 3, was produced as described below. First, 87.5 g of component 1), 542.5 g of component 3), 490 g of component 4) and 350 g of component 5) were thoroughly mixed to yield a dusting powder. 2,730 g of component 2) was placed in a centrifugal fluidized coating granulator (produced by Freund Industrial Co., Ltd., CF-3600) and coated with the above dusting powder, while 1,120 g of an aqueous solution of 28 g of component 6) was sprayed.

Further, 143.5 g of component 3), 161 g of component 4) and 157.5 g of component 5) were thoroughly mixed to yield a dusting powder, which was then used for coating subsequent to coating with the above dusting powder to yield spherical granules.

These spherical granules were vacuum dried at 40° C. for 16 hours and sieved through a round sieve to yield 710 to 1,000μ principal agent granules.

4,020 g of said principal agent granules were placed in a fluidized granulator drier (produced by Powrex Corporation) and coated with 9,470.0 g of a suspension containing 879.0 g of component 7) (2,930.0 g as 30% methacrylic acid copolymer emulsion), 264.0 g of component 8), 87.0 g of component 9) and 39.0 g of component 10) to yield enteric granules.

4,936.4 g of these enteric granules, 14.0 g of component 11) and 5.6 g of component 12) were mixed using a tumbler mixer (produced by Showa Kagaku Kikai Kosakusho) to yield mixed granules, 4,956.0 g of which was filled in No. 3 gelatin capsules using a capsule filling machine (produced by Zanasi Co.) to yield capsule E.

REFERENCE EXAMPLE 13

In the same manner as in Reference Example 12, capsules F and G, having the respective compositions per capsule shown in Table 3, were produced.

REFERENCE EXAMPLE 14

Using the mixed granules obtained when capsule G was produced in Reference Example 13, and No. 1 gelatin capsules, capsule H, containing 20 mg of compound A per capsule, was obtained.

TABLE 3

(Compound A: N-demethyl-N-isopropyl-8,9-anhydroerythromycin A-6,9-hemiacetal)

| Composition (per capsule) | Capsule E | Capsule F | Capsule G |
|---|---|---|---|
| [Principal agent granules] | | | |
| 1) Compound A | 2.5mg | 5.0mg | 10.0mg |
| 2) Sucrose-starch spherical granules | 78.0 | 78.0 | 78.0 |
| 3) Purified sucrose | 19.6 | 19.1 | 16.1 |
| 4) Corn starch | 18.6 | 16.6 | 14.6 |
| 5) Low substitutional hydroxypropyl cellulose | 14.5 | 14.5 | 14.5 |
| 6) Hydroxypropyl cellulose | 0.8 | 0.8 | 0.8 |
| Subtotal [Enteric granules] | 134.0 | 134.0 | 134.0 |
| Principal agent granules | 134.0 | 134.0 | 134.0 |
| 7) Methacrylic acid copolymer LD | 29.3 | 29.3 | 29.3 |
| 8) Talc | 8.8 | 8.8 | 8.8 |
| 9) Macrogol 6000 | 2.9 | 2.9 | 2.9 |
| 10) Polysorbate 80 | 1.3 | 1.3 | 1.3 |
| Subtotal [Mixed granules] | 176.3 | 176.3 | 176.3 |
| Enteric granules | 176.3 | 176.3 | 176.3 |
| 11) Talc | 0.5 | 0.5 | 0.5 |
| 12) Light silicic anhydride | 0.2 | 0.2 | 0.2 |
| Subtotal [Capsular preparation] | 177.0 | 177.0 | 177.0 |
| Mixed granules | 177.0 | 177.0 | 177.0 |
| 13) No. 3 gelatin capsule | 50.0 | 50.0 | 50.0 |
| Total | 227.0 | 227.0 | 227.0 |

The acid resistance in solution 1, dissolution in solution 2, and other preparation properties of the capsular preparations obtained were good.

INDUSTRIAL APPLICABILITY

Because the production method of the present invention makes it possible to produce erythromycin derivatives, especially 8,9-anhydroerythromycin A-6,9-hemiacetal derivatives (e.g. N-demethyl-N-isopropyl-8,9-anhydroerythromycin A-6,9-hemiacetal and N-demethyl-N-ethyl-8,9-anhydroerythromycin A-6,9-hemiacetal) at high yield and high purity, with suppressed byproduct formation, it provides a very advantageous process for industrial mass production of such derivatives, which are useful as pharmaceuticals as described above.

We claim:

1. A method of producing a substantially pure crystal of an 8,9-anhydroerythromycin A-6,9-hemiacetal derivative represented by formula (VI):

(VI)

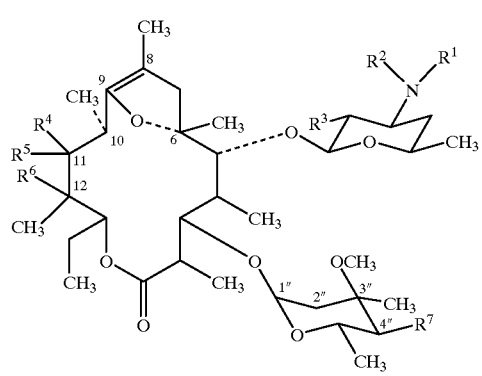

wherein $R^1$ and $R^2$, whether identical or not, represent an alkyl having 1 to 6 carbon atoms, an alkenyl having 2 to 6 carbon atoms or an alkynyl having 2 to 6 carbon atoms; $R^3$ represents hydrogen or a hydroxyl group; one of $R^4$ and $R^5$ represents hydrogen and the other represents a hydroxyl group, or $R^4$ and $R^5$ bind together to represent O=; $R^6$ represents hydrogen or a hydroxyl group which may be substituted; $R^7$ represents hydrogen or a hydroxyl group; or a salt thereof, said method comprising recrystallizing a crude crystal of said 8,9-anhydroerythromycin A-6,9-hemiacetal derivative or a salt thereof as a salvation product from an isopropanol/water mixed solvent wherein each of the isopropanol and the water is used in a volume about 1 to 20 times, relative to said 8,9-anhydroerythromycin A-6,9-hemiacetal derivative or a salt thereof, and the ratio of the isopropanol to the water is about 1:0.5 to 1:3.

2. A method of claim 1, wherein the crude crystal of the 8,9-anhydroerythromycin A-6,9-hemiacetal derivative is represented by the formula:

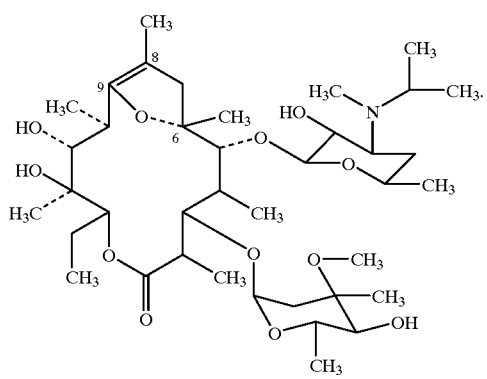

3. A method of claim 2, wherein the crude crystal of the 8,9-anhydroerythromycin A-6,9-hemiacetal derivative or a salt thereof is produced by reacting the compound of the formula (I):

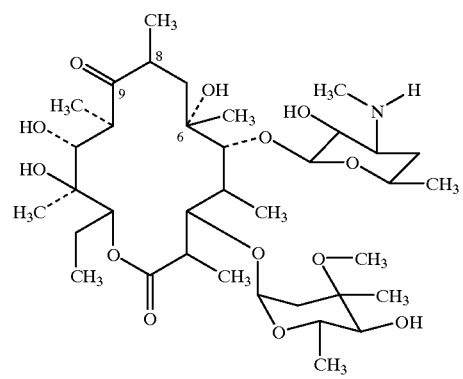

or a salt thereof, with an isopropylating agent and followed by treating under acidic conditions.

4. A method of claim 1, wherein the crude crystal of the 8,9-anhydroerythromycin A-6,9-hemiacetal derivative is represented by the formula:

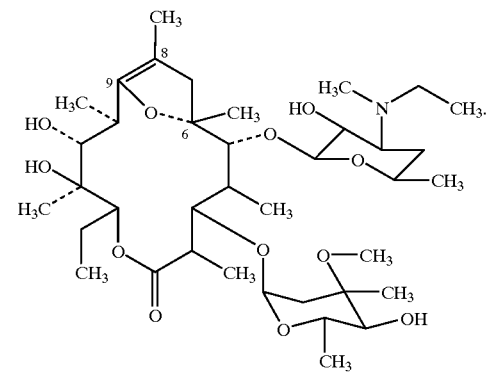

5. A method of claim 4, wherein the crude crystal of the 8,9-anhydroerythromycin A-6,9-hemiacetal derivative or a salt thereof is produced by treating the compound of the formula (I):

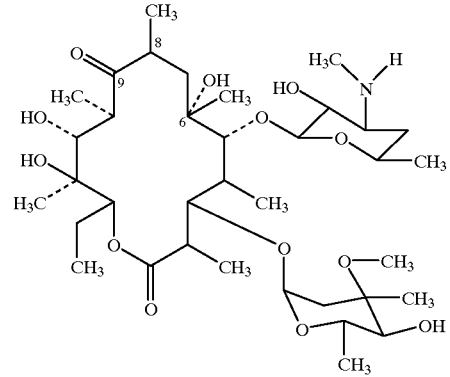

or a salt thereof, under acidic conditions and followed by reacting with an ethylating agent.

6. A method of claim 1, wherein the hydroxyl group that may be substituted is a hydroxyl group that may be substituted by an alkyl having 1 to 6 carbon atoms, an alkenyl having 2 to 6 carbon atoms or an alkynyl having 2 to 6 carbon atoms.

7. A method of claim 1, wherein the isopropanol is used in a volume about 2 to 5 times relative to said 8,9-anhydroerythromycin A-6,9-hemiacetal derivative or a salt thereof.

8. A method of claim 1, wherein the water is used in a volume about 2 to 10 times, relative to said 8,9-anhydroerythromycin A-6,9-hemiacetal derivative or a salt thereof.

9. A method of claim 1, wherein the ratio of the isopropanol to the water is about 1:1 to 1:2.

* * * * *